(12) United States Patent
Divi et al.

(10) Patent No.: US 8,378,110 B1
(45) Date of Patent: Feb. 19, 2013

(54) PROCESS FOR THE PREPARATION OF (R, S)-NICOTINE

(71) Applicants: Murali Krishna Prasad Divi, Hyderabad (IN); Gundu Rao Padakandla, Hyderabad (IN); Mysore Aswatha Narayana Rao, Hyderabad (IN); Hari Babu Katta, Hyderabad (IN)

(72) Inventors: Murali Krishna Prasad Divi, Hyderabad (IN); Gundu Rao Padakandla, Hyderabad (IN); Mysore Aswatha Narayana Rao, Hyderabad (IN); Hari Babu Katta, Hyderabad (IN)

(73) Assignee: Divi's Laboratories, Ltd. (IN)

( * ) Notice: Subject to any disclaimer, the term of this patent is extended or adjusted under 35 U.S.C. 154(b) by 0 days.

(21) Appl. No.: 13/647,031

(22) Filed: Oct. 8, 2012

Related U.S. Application Data

(62) Division of application No. 13/080,995, filed on Apr. 6, 2011.

(30) Foreign Application Priority Data

Feb. 14, 2011 (IN) .............................. 407/CHE/2011

(51) Int. Cl.
*C07D 401/06* (2006.01)
(52) U.S. Cl. .................................................. 546/278.4
(58) Field of Classification Search ................ 546/278.4
See application file for complete search history.

(56) References Cited

PUBLICATIONS

Svante Brandange and Lars Lindblom, Department of Organic Chemistry, Arrhenius Laboratory, University of Stockholm, S-104 05 Stockholm Sweden, N-Vinyl as N-H-Portecting Group, a Convenient Synthesis of Myosminem Acta Chem. Scand B30(1976) No. 1—Sep. 1975.
Michael C. Detraglia and Andrew M. Tometsko, Separation of D-(+)-Nicotine Froma Racemic Mixture of Stereospecific Degradation of the L-(-)Isomer With *Pseudomonas putida*, Applied and Environmental Microbiology, May 1980, p. 1067-1069.
Michael B. Smith, et al. A New Lactam Protecting Group, Chemistry Letters 1992, 247-250.
Wilfried Hatton, et al. Synthesis of Four Racemic Nicotine Isotopomers Doubly Labelled With Stable Isotope, J. Label Compd. Radiopharm 2009, pp. 117 to 122.
Paul G. Haines, Abner Eisner and C.F. Woodward, Chemical Reactivity of Myosmine, JACS 1945, 1258-262.
Jeffrey P. Jones, William F. Trager and Timothy J. Carlson, The Binding and Regioselectivity (S)-Nicotine With Cytochrome P-450cam, Parallel Experimental and Theoretical Studies, JACS 1993, 115, 381-387.
Mario D. Aceto, et al. Optically Pure (+)Nicotine From (+)-Nicotine and Biological Comparisions With (-)Nicotine, Department of Pharmacology, Medical College of Virginia, Richmond, virginia 23298, Journal of Medicinal Chemistry, 1979, vol. 22, No. 2 174-177.
Charles G. Chavdarian, et al. Synthesis of Optically Active Nicotinoids, J. Org. Chem 1982, 1069-1073.
Peyton Jacob, III, Resolution of (+)-5-Bromonornicotine. Synthesis of (R)-and(S)-Nornicotine of High Enantiomeric Purity, J. Org. Chem. 1982, 47 4165-4167.
Tae Woo Kwon, et al. Asymmetric synthesis of (s)-4-Aminohex-5-enoic Acid: A Potent Inhibitor of 4-Aminobutyrate-2-oxoglutarate Aminotransferase, J. Org. Chem, 1992, 6169-6173.
Pierre Dubon, et al Enantioselective syntheses of 2-Substituted Pyrrolidines from Allylamines by Domino Hydroformylation-condensation: Short syntheses of (s)-Nicotine and the Alkaloid 225 C, Synlett 2009, No. 9 pp. 1413-1416.
Edward R. Bowman, et al. A Convenient Method for the Preparation of Racemic Nicotine, Synethic Communications, 1982, 871-879.
Teck-Peng Loh, A novel reductive aminocyclization for the syntheses of chiral phrrolidines, stereoselective syntheses of (s)-nornicotine and 2-2' pyrrolidyl)-pyridines, Tetrahedron Letters 40 (1999) 7847-7850.
Leo S. Bleicher, et al. A practical and Efficient synthesis of the Selective Neuronal Acetylcholine-Gated Ion Channel Agonist (S)(-)5-Ethynyl-3-(1-methyl-2-pyrrolininyl) Pyridine Maleate (SIB-1508y), J. Org. Chem 1998, 63, 1109-1118.
Tobin J. Dickerson, et al. Aqueous Aldol Catalysis by a Nicotine Metaboite, J. Am. Chem. Society 2002, 124, 3220-3221.
European Search Report of DP 12 15 4900 dated Apr. 12, 2012.
D. Spitzner, Eine Einfache synthese von Pyridinalkoloiden, Synthesis, Communication 242-243, Nov. 9, 1976.

*Primary Examiner* — Patricia L Morris
(74) *Attorney, Agent, or Firm* — Caesar, Rivise, Bernstein, Cohen & Pokotilow, Ltd.

(57) ABSTRACT

A process for (R,S)-nicotine is described. Condensation of 1-(but-1-enyl)pyrrolidin-2-one with nicotinic acid ester gave 1-(but-1-enyl)-3-nicotinoylpyrrolidin-2-one which on treatment with an acid and a base gave myosmine. Myosmine was converted to (R,S)-nicotine by reduction followed by N-methylation.

3 Claims, No Drawings

PROCESS FOR THE PREPARATION OF (R, S)-NICOTINE

CROSS-REFERENCE TO RELATED APPLICATIONS

This application claims priority from India Application Serial No. 407/CHE/2011, filed on Feb. 14, 2011, entitled A PROCESS FOR THE PREPARATION OF (R,S)-NICOTINE, which application is assigned to the same assignee as this application and whose disclosure is incorporated by reference herein.

FIELD OF THE INVENTION

The present invention describes a synthetic process for the preparation of (R,S)-nicotine.

BACKGROUND OF THE INVENTION

Nicotine, (S)-3-(1-methyl-2-pyrrolidinyl)pyridine, is an alkaloid found mainly in tobacco. Smoking of tobacco results in nicotine dependence and is habit forming. Smoking has also been associated with disease of lungs including malignant growth. There is a world-wide recognition of harmful effects of smoking. Unfortunately habitual smokers find it very hard to achieve abstinence from smoking. Further dependence on nicotine comes in the way of any effort to control smoking. To overcome this formidable issue, products containing small amounts of nicotine have been developed and are being promoted as substitutes for traditional smoking products like cigars and cigarettes. Treating nicotine dependence requires therapeutic use of nicotine. Nicotine is given to patients through dermal patches, gums, creams, lozenges, nasal sprays or electric cigarettes to wean them away from smoking. Nicotine is also therapeutically used in treating certain medical conditions such as attention deficit disorder, Tourette's syndrome, schizophrenia, Alzheimer's disease, Parkinsonism etc.

The main source of nicotine is tobacco. Nicotine isolated from tobacco contains many related minor alkaloids as impurities in addition to impurities formed through degradation. European Pharmacopoeia monograph on nicotine prescribes limits for anatabine, anabasine, cotinine, myosmine, β-nicotyrine, nicotine-N-oxide and nornicotine impurities, with a maximum of 0.3% for each of these but total being limited to not more than 0.8%. British Pharmacopoeia also mentions anatabine, cotinine, myosmine, β-nicotyrine, nicotine-N-oxide as impurities. Although the USP does not mention specific impurities, a limit of 1% for all the impurities and not more than 0.5% for any one impurity is prescribed. The impurities present in natural nicotine vary depending on the geographical source of tobacco and the season in which it is collected. It is difficult to remove these impurities since they are closely related. Thus the pharmacopoeias recognize the variations in quality and quantity of impurities in natural nicotine.

It was envisaged that nicotine obtained from synthetic source will be free from the impurities present in natural nicotine. Further, synthetic nicotine produced by a validated process with well characterized impurity profile should be a superior API compared to natural nicotine with its varying impurity profile.

Several synthesis of (S)-nicotine are reported in the literature. Chiral center has been created by using expensive chiral intermediates such as prolinol (J. Org. Chem. 1982, 41, 1069-1073), pivaloyl-β-D-galactosylamine (Tetrahedron Letters, 1999, 40, 7847-7650), or using chiral catalyst (Synlett 2009, 9, 1413-1416). However, these methods are expensive and are not suitable for industrial production.

SUMMARY OF THE INVENTION

Since the enantioselective synthesis is too expensive on an industrial scale, synthesis of (R,S)-nicotine followed by resolution and racemisation of unwanted (R)-nicotine was explored.

The resolution of (R,S)-nicotine is reported in the literature. Aceto et al have resolved the racemic nicotine using d-tartaric acid (J. Med. Chem. 1979, 22, 174-177). DeTraglia and Tometsko have resolved (R,S)-nicotine using Pseudomonas putida cultures (Applied and Environmental Microbiology, 1980, 39, 1067-1069). Racemization of (S)-nicotine is also reported in the literature (Synthetic Communications, 1982, 12, 871-879)

We have developed a new and efficient process for the synthesis of (R,S)-nicotine. Together with the known methods for its resolution and racemization of the unwanted isomer, this process provides an attractive and economical method for the production of synthetic (S)-nicotine. It will be an alternative to natural nicotine, which has several disadvantages as mentioned earlier.

DETAILED DESCRIPTION OF THE INVENTION

The process for the preparation of (R,S)-nicotine is outlined in Scheme 3 below:

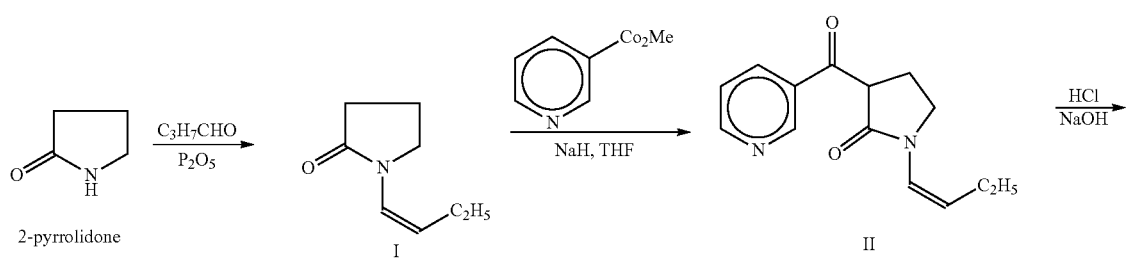

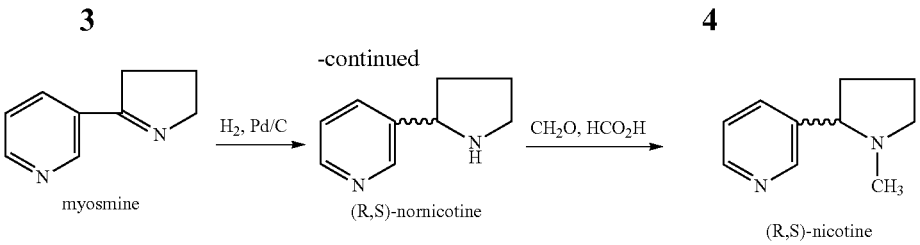

myosmine     (R,S)-nornicotine     (R,S)-nicotine

The most convenient way to prepare (R,S)-nicotine is through myosmine (Scheme-3). Myosmine is hydrogenated to (R,S)-nornicotine, which on N-methylation gives (R,S)-nicotine.

Myosmine has been prepared by condensing N-vinylpyrrolidone with ethyl nicotinate. (*Acta. Chem. Scand. B.* 1976, 30, 93). However, preparation of N-vinylpyrrolidone involves use of acetylene gas at high temperature and pressure. N-vinylpyrrolidone is lachrymatory and irritating to the skin, lungs, and eyes. It is known to cause corneal opacity. Our efforts to find a safer alternative resulted in the selection of N-(1-Butenyl)-2-pyrrolidone (I, scheme-3) which has not been used till now to prepare myosmine. N-(1-butenyl)-2-pyrrolidone (I) is a stable, colorless liquid and is not lachrymatory. Its preparation, as reported in the literature, involves reacting butanal with 2-pyrrolidone in a solvent using p-toluenesulfonic acid as a condensing agent (*Chemistry Letters,* 1992, 247-250). Sulfonic acid and its esters are considered to be potential alkylating agents that exert genotoxic effects. Because of this, use of p-toluenesulfonic acid is avoided in industrial processes. Earlier literature describes several other catalysts such as sulfuric acid and neutral or acidic alumina for condensing the aldehyde with 2-pyrrolidone (*Chemistry Letters,* 1992, 247-250). In our hand, none of these catalysts gave satisfactory results. Kwon et al. had condensed (S)-ethyl pyroglutamate with butanal using phosphorous pentoxide as catalyst (*J. Org. Chem.* 1992, 57, 6169-6173) to obtain (S)-ethyl-N-(1-butenyl)pyroglutamate. When we tried phosphorus pentoxide, it was found to be an excellent condensing agent and gave I in good yields. Phosphorus pentoxide is soluble in water and can be removed by alkali wash during workup to give phosphate salt, which is not injurious to health on dilution. Phosphate salts are routinely used as fertilizers and in food industry. In the next stage, I was condensed with methyl nicotinate using sodium hydride in a solvent such as THF or DMF to obtain 1-(but-1-enyl)-3-nicotinoylpyrrolidin-2-one (II) in good yields. To our knowledge II is a new molecule and is not reported in the literature till now. Reaction of II with strong mineral acid such as hydrochloric acid under heating resulted in the deprotection of amide nitrogen, followed by decarboxylation to give a primary amine intermediate which on treating with base resulted in cyclization to give myosmine. This is the first report of the preparation of myosmine starting from II. Catalytic hydrogenation of myosmine resulted in (R,S)-nornicotine. Haines et al used palladium oxide in ethanol to reduce myosmine to (R,S)-nornicotine and isolated (R,S)-nornicotine only as picrate salt (*J. Amer. Chem. Soc.,* 1945, 1258-1260). Jacob used sodium borohydride in methanol-acetic acid to reduce a related compound, 5-bromomyosmine to obtain racemic 5-bromo-nornicotine (*J. Org. Chem.,* 1982, 47, 4165-4167). Hatton et al. used palladium on activated carbon in methanol to reduce myosmine labeled with stable isotope, [6-$^2$H]-myosmine to [6-$^2$H]-nornicotine (*J. Label Compd. Radiopharm.* 2009, 52, 117-122). After screening a number of catalysts, we selected palladium on carbon with methanol as medium. After general workup, the pure (R,S)-nornicotine was isolated by high vacuum distillation in high yields and high purity. Conversion of (R,S)-nornicotine to (R,S)-nicotine was carried out by N-methylation using formaldehyde and formic acid as reported in the literature (*J. Amer. Chem. Soc.,* 1993, 115, 381-387).

The embodiments of the present invention are illustrated in the following examples, which are not intended in any way to limit the scope of the invention.

EXAMPLES

Example-1

A. Preparation of 1-(but-1-enyl)pyrrolidin-2-one (I)

A solution of 2-pyrrolidone (50 g, 0.588 mol), butanal (42.4 g, 0.588 mol) and $P_2O_5$ (2 g, 0.014 mol) in 300 ml toluene, were refluxed together for 10 hours using Dean-Stark apparatus to collect liberated water. The resulting solution was cooled and washed with 5% solution of sodium bicarbonate and dried over anhydrous sodium sulphate. After removing the solvent under reduced pressure, 1-(but-1-enyl)pyrrolidin-2-one (I) was obtained by distillation as a liquid. (68.2 g, 83.2%). $^1$H NMR (CDCl$_3$): δ 1.02 (3H, t), 2.03-2.15 (4H, m), 2.45 (2H, t), 3.5 (2H, t), 5.01 (1H, m), and 6.85 (1H, d). $^{13}$C-NMR (CDCl$_3$): δ 172.52, 122.91, 113.8, 45.09, 31.07, 23.03, 17.27, and 14.27. IR: 2962, 2930, 1698, 1663, 1253 Cm$^{-1}$.

B. Preparation of 1-(but-1-enyl)-3-nicotinoyl-pyrrolidin-2-one (II)

Sodium hydride (8.63 g, 0.36 mol of 60% dispersion in a mineral oil) was washed with toluene to remove mineral oil. To this 20 ml of dimethylformamide (DMF), 1-(but-1-enyl) pyrrolidin-2-one (25 g, 0.1798 mol) and a solution of methyl nicotinate (20.94 g, 0.152 mol) in 15 ml of DMF were added. The reaction mixture was heated at 90° C. for 2 hrs. DMF was partially removed under reduced pressure, 50 ml water added, further cooled to 0-10° C. and pH adjusted to 7 using HCl. The reaction mixture was extracted with ethyl acetate and dried over Na$_2$SO$_4$. After removing the solvent under reduced pressure a yellow solid was obtained, which on recrystallisation with diisopropyl ether gave 1-(but-1-enyl)-3-nicotinoyl-pyrrolidin-2-one (II, 35.1 g, 94% yield), 95% HPLC, M.R: 65-66° C. $^1$H NMR (CDCl$_3$): δ 9.3 (1H, d), 8.8 (1H, d), 8.41 (1H, dt), 7.4 (1H, m), 6.76 (1H, d), 5.0 (1H, m), 4.5 (1H, m), 3.57-3.67 (2H, m), 2.7 (1H, m), 2.3 (1H, m), 2.0 (2H, m), and 1.0 (3H, t). $^{13}$C-NMR (CDCl$_3$): δ 194.4, 167.1, 153.7, 150.4, 137.0, 134.4, 131.2, 123.3, 114.9, 51.7, 44.2, 23.2, 22.3, and 14.26. IR: 2966, 2937, 2855, 2847, 1631, 1613, 1489 Cm$^{-1}$.

C. Preparation of Myosmine

A mixture of 1-(but-1-enyl)-3-nicotinoylpyrrolidin-2-one (II), (40 g, 0.1639 mol), 50 ml water and 85 ml HCl were refluxed together for 12 hrs. The reaction mixture was cooled to room temperature, washed with 50 ml×2 ethyl acetate, further cooled to 0° C. and pH adjusted to >13 using NaOH. The reaction mixture was extracted with 100 ml×3 of dichloromethane and the extract dried over $Na_2SO_4$. After removing the solvent under reduced pressure, the crude solid obtained was purified by high vacuum distillation to give colorless solid myosmine (16.75 g, 70%). $^1$H NMR ($CDCl_3$): δ 2.05 (2H, m), 2.94 (2H, t), 4.06 (2H, t), 7.34 (1H, dd), 8.18 (1H, dt), 8.64 (1H, dd), and 8.99 (1H, d). $^{13}$C-NMR ($CDCl_3$): δ 170.56, 151.1, 149.1, 134.6, 130.0, 123.3, 61.5, 34.7, and 22.5. IR: 2961, 1620, and 1590 $Cm^{-1}$.

D. Preparation of Nornicotine

Myosmine (32 g, 0.219 mol) was dissolved in 150 ml of methanol and hydrogenated at atmospheric pressure with 1.3 g of 10% palladium on carbon as catalyst. After 5 hours the mixture was filtered and the filtrate was concentrated to get a brown solid (32 g, 94.9% purity by GC). It was further purified by vacuum distillation at 0.1 mm Hg to get pure nornicotine (27.46 g, 84.7% yield, 97.5% purity by GC). $^1$H NMR ($CDCl_3$): δ 1.66-2.72 (2H, m), 3.0 (2H, m), 4.13 (1H, t), 7.24 (1H, m), 7.69 (1H, dt), 8.46 (1H, dd), and 8.59 (1H, d). $^{13}$C-NMR ($CDCl_3$): δ 148.4, 148.1, 140.16, 134.1, 123.3, 60.0, 46.8, 34.2, and 25.4. IR: 3291, 2960, 1641, 1578 $Cm^{-1}$.

E. Preparation of (R,S)-Nicotine

To a solution of nornicotine (50 g 0.338 mol) in 100 ml water a mixture of 37% formaldehyde (49.7 g, 1.656 mol) and 85% formic acid (37.26 g 0.81 moles) was added and stirred at 85° C. for 20 hrs. The reaction was cooled and pH adjusted to >13 using NaOH, extracted with dichloromethane (100 ml×3) dried over $Na_2SO_4$ and solvent removed completely to get crude oil (52.5 g, 94.33% purity by GC). It was further purified by high vacuum distillation at 0.1 mm Hg to obtain colorless (R,S)-nicotine (44.54 g, 81.3% yield, 99.1% purity by GC). $^1$H NMR ($CDCl_3$): δ 1.72-2.0 (3H, m), 2.1 (3H, s), 2.25 (1H, m), 2.3 (1H, m), 3.08 (1H, m), 3.23 (1 h, t), 7.25 (1H, m), 7.69 (1H, dt), and 8.5 (2H, m). $^{13}$C-NMR ($CDCl_3$): 149.71, 148.76, 139, 134.97, 123.7, 68.9, 57.1, 40.5, 35.5, and 22.83. IR: 3233, 1642, and 1402 $Cm^{-1}$.

Example-2

Preparation of Myosmine from I

Sodium hydride (17.26 g, 072 mol of 60% dispersion in a mineral oil) was washed with toluene (25 ml×2) to remove mineral oil and added to 25 ml of DMF. To this a solution containing 1-(but-1-enyl)-pyrrolidin-2-one (1.50 g, 0.3597 mol) and methyl nicotinate (41.8 g, 0.3057 mol) in 50 ml of DMF was added. The reaction mixture was heated to 90° C. for 2 hrs. DMF was partially removed under reduced pressure and 100 ml water and HCl (165 ml) were added. The reaction mixture was heated to 110° C. for 12 hr, cooled and washed with ethyl acetate (50 ml×2). The aqueous layer was cooled to 0° C., pH adjusted to about 14 using NaOH, extracted with dichloromethane (100 ml×4), the extract dried over $Na_2SO_4$, the solvent removed completely and the crude solid was purified by high vacuum distillation to get myosmine (34.38 g, 77.2% yield, 98.5% purity by GC).

We claim:
1. A process for the preparation of a compound I-(1-butenyl)-3-nicotinoylpyrrolidine-2-one of the formula:

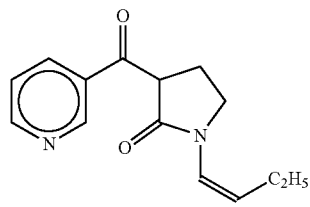

comprising: condensing nicotinic acid ester with N-(1-butenyl)-2-pyrrolidone in a suitable solvent using a base.

2. A process as in claim 1 wherein the solvent used is dimethylformamide or tetrahydrofuran.

3. A process as in claim 1 wherein the base used is sodium hydride.

* * * * *